(12) United States Patent
Yoneda

(10) Patent No.: US 6,783,257 B2
(45) Date of Patent: Aug. 31, 2004

(54) LIGHTING APPARATUS FOR INSPECTION OF AN OBJECT

(75) Inventor: Kenji Yoneda, Kyoto (JP)

(73) Assignee: CCS Inc., Kyoto (JP)

(*) Notice: Subject to any disclaimer, the term of this patent is extended or adjusted under 35 U.S.C. 154(b) by 1 day.

(21) Appl. No.: 10/255,012

(22) Filed: Sep. 25, 2002

(65) Prior Publication Data

US 2003/0058631 A1 Mar. 27, 2003

(30) Foreign Application Priority Data

Sep. 25, 2001 (JP) ........................................ 2001-290296

(51) Int. Cl.[7] ................................................ F21V 7/04
(52) U.S. Cl. ........................ 362/247; 362/33; 362/240; 362/248
(58) Field of Search ................................. 362/240, 231, 362/33, 800, 293, 31, 247, 248; 359/385, 387; 348/370, 92, 87

(56) References Cited

U.S. PATENT DOCUMENTS 5,187,611 A * 2/1993 White et al. ................ 359/599
5,369,492 A * 11/1994 Sugawara ................... 356/394
5,461,417 A * 10/1995 White et al. ................ 348/131

FOREIGN PATENT DOCUMENTS

JP 119-434 4/1994
JP 510-053 10/1996

* cited by examiner

Primary Examiner—Alan Cariaso
Assistant Examiner—Ali Alavi
(74) Attorney, Agent, or Firm—Kirschstein, et al.

(57) ABSTRACT

A small or size-reduced lighting apparatus for an inspection is disclosed. The lighting apparatus for an inspection comprises a lighting portion 3 having a large number of light emitters 2 provided circularly, and a guide member 5 including a large number of reflecting portions 6 for reflecting a part of lights emitted from the light emitters 2 and guiding the same light to an inspection object provided in a lower position, wherein the light for inspection which has been applied on and reflected by the inspection object can be fetched through the apertures among the reflecting portions.

5 Claims, 5 Drawing Sheets ents mounted on a substrate in a factory or the like, for example.

LIGHTING APPARATUS FOR INSPECTION OF AN OBJECT

BACKGROUND OF THE INVENTION

1. Field of the Invention

The present invention relates to a lighting apparatus for an inspection which is used for irradiating a light on a product to be an inspection object and inspecting the external appearance and scratches of the product, and furthermore, the inspections of the quality of soldering of an electronic components mounted on a substrate in a factory or the like, for example.

2. Prior Art

Examples of the conventional lighting apparatus for an inspection include a coaxial lighting apparatus for coaxially irradiating a light on a CCD camera 7 as shown in FIG. 6, for example. In a casing 21 of a lower end opening type having an upper end provided with an opening 20 for the CCD camera 7, the coaxial lighting apparatus comprises a half mirror 23 having such an attitude as to be inclined by 45 degrees with respect to an optical axis 22 of the CCD camera 7, a large number of light emitting diodes 24 provided facing the lateral side of the half mirror 23 and mounted in the same plane for irradiating a light toward the half mirror 23 in a orthogonal direction to the optical axis 22, and a diffusion plate 25 positioned ahead of the light emitting diode 24. In the case in which an inspection object 4 is for inspection by using the lighting apparatus for an inspection thus constituted, the inspection object 4 is disposed below the lighting apparatus for an inspection. A light emitted from the light emitting diode 24 is diffused by the diffusion plate 25, reflected by the half mirror 23 and thus directed downward, thereby illuminating the inspection object 4. The light applied on and reflected by the inspection object 4 is transmitted through the half mirror 23 and then received by the CCD camera 7 through the opening 20, and the light thus received is subjected to an image processing by an image processing device which is not shown, for example, so that the quality of an image can be determined by a computer.

In the lighting apparatus for an inspection, however, the half mirror 23 having the attitude of a 45-degree inclination is disposed. Therefore, there is a drawback that the size of the whole apparatus is increased in a vertical direction.

Moreover, a space is required for disposing the diffusion plate 25 ahead of the light emitting diode 24. For this reason, there is a drawback that the size of the whole apparatus is also increased in a horizontal direction.

In consideration of the circumstances described above, it is an object of the present invention to provide a lighting apparatus for an inspections which can be reduced in size.

SUMMARY OF THE INVENTION

In order to solve the above-mentioned problems, the present invention provides a lighting apparatus for an inspection comprising: lighting means having a large number of light emitters, and guide means including a large number of reflecting portions for reflecting a part of lights emitted from the light emitters and directing the part of lights to an inspection object provided in a lower position, wherein the light for inspection which is applied on and reflected by the inspection object can be received through the apertures among the reflecting portions of the guide member.

Accordingly, by way of circularly disposing the light emitters, consequently, a large number of light emitters can be provided. The light emitted from the light emitters is reflected by the reflecting portion of the guide means, and the light thus reflected is directed to the inspection object provided in a lower position. The inspection object on which the light is irradiated is visually observed through apertures among the reflecting portions of the guide member or an image is picked up by image input means such as a CCD camera to carry out an image processing so that the inspection object can be inspected.

The guide means may be formed of a flat and transparent light guiding plate. Consequently, it is possible to reduce the size of the guiding means in a vertical direction. Moreover, a surface on an opposite side to the inspection object of the light guiding plate is caused to include a dotted pattern with white paint spots or the like grid pattern directly thereon or over a transparent film provided on the surface, or a concavo-convex processing is carried out directly over the surface or over the transparent film provided on the surface, thereby constituting a light diffusing property with the reflecting portion. Consequently, the amount of light irradiation can be uniform in any part of the inspection object. The concavo-convex processing includes embossing capable of forming an emboss pattern having a high concavo-convex degree and graining capable of forming a grain, that is, fine concavo-convex portions such as a so-called wrinkle, pear-skin pattern or the like. A rough surface provided with fine concavo-convex portions is formed by the graining in place of the embossing. Consequently, there is an advantage that the light can be diffused at a small angle, for example, the generation of a glitter in a display screen can be prevented.

By covering the upper surface of the reflecting portion with a layer for absorbing a light, it is possible to avoid such a situation that the light is diffusively reflected by the upper surface of the reflecting portion and recognition is carried out by the image input means with difficulty. While it is preferable that all the lights should be absorbed, it is also possible to permit the case in which all the lights cannot be absorbed but a part of the lights which cannot be absorbed is diffusively reflected.

The light emitting diodes are provided on an outer peripheral edge of the light guiding plate on almost the same level with the light guiding plate in such a state that the top of the light emitting surface is directed toward a central part of the light guiding plate. Consequently, it is possible to dispose a part or all of lighting fields of the light emitting diodes to overlap with the light guiding plate in a horizontal direction. As compared with the case in which the light emitting diodes are provided below the light guiding plate (in a little overlapping position), the size of the lighting apparatus for an inspection can be more reduced in a vertical direction.

Areas of the reflecting portions positioned on a side separated from image input means provided to fetch the light for inspection and to pick up an image are more reduced than those of the other reflecting portions.

For example, in the case in which the reflecting portion having the same area is provided over the whole area of the guide means to pick up an image by a camera to be the image input means, a visual field in the central part of the lens of the camera is darkened and a visual field in an outer peripheral edge portion excluding the central part of the lens becomes bright so that the brightness of the light fetched into the camera is varied depending on the portions of the lens. By setting the areas of the reflecting portions provided apart from the image input means to be smaller than those of the other reflecting portions as described above, consequently, it is possible to cause any portion of the lens to have a visual field having the same brightness. By gradually (stepwise) reducing the area of the reflecting portion from one corresponding to the center of the lens toward the others corresponding to the outer peripheral edge, it is possible to cause the visual field to have the same brightness in all the portions of the lens still more.

DESCRIPTION OF THE PREFERRED EMBODIMENT

Figure 1A:
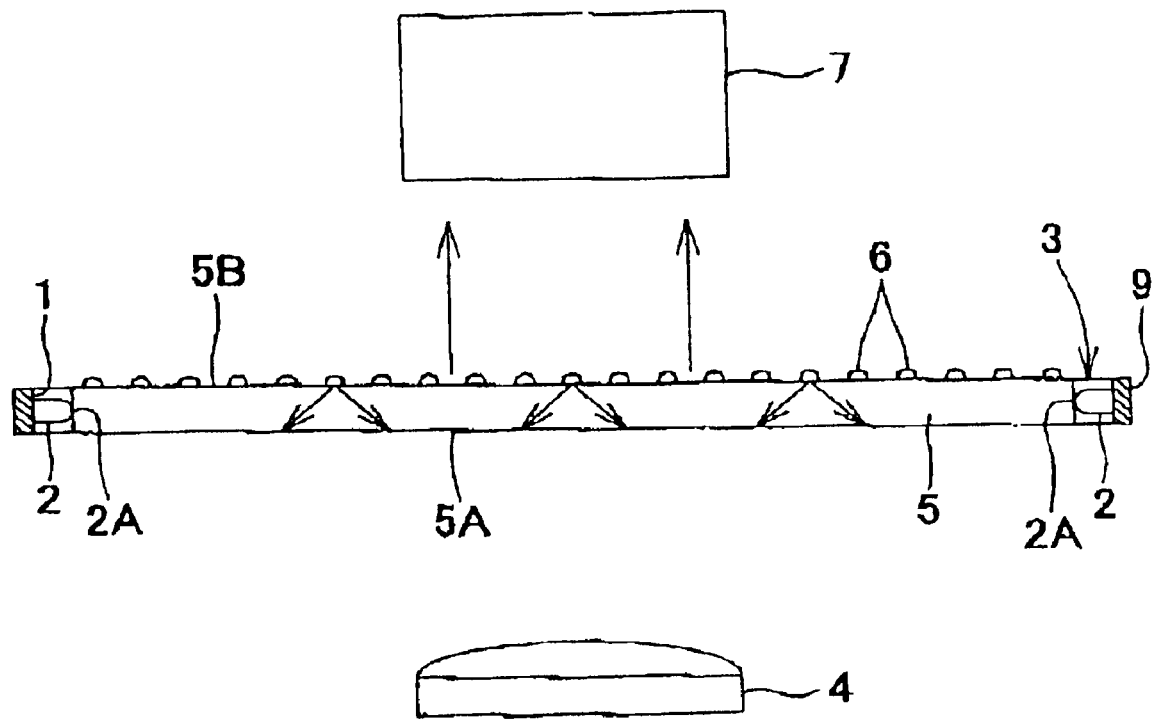
FIG. 1A is a longitudinal sectional view showing a lighting apparatus for an inspection and FIG. 1B is a plan view showing a light guiding plate.

FIG. 1A shows a lighting apparatus for an inspection according to the present invention. The lighting apparatus for an inspection comprises a lighting portion 3 in which a large number of light emitting diodes 2 as light emitters are provided circularly with the tops of the lighting surfaces 2A thereof directed toward the center of a circle, a flat and transparent disc type light guiding plate 5 to be a guide member for fetching lights from the light emitting diodes 2 and guiding a part of the lights to an inspection object 4 provided below the guiding plate 5, and a large number of reflecting portions 6 of the upper surface of the light guiding plate 5 for reflecting a part of the fetched lights and directing the same light downward, whereby the guided light for an inspection is applied on and reflected by the inspection object 4, transmitted through a surface area or apertures among the reflecting portions, and can be fetched into a CCD camera 7 as image input means provided above the light guiding plate 5. A large number of light emitting diodes 2 are provided on the outer peripheral edge of the light guiding plate 5 at the same level with the light guiding plate 5, that is, to set the middle level in the vertical direction (the thickness direction) of the light guiding plate 5 matches with the optical axes of the light emitting diodes 2 and the top of each lighting surface 2A is directed to the center of the light guiding plate 5. Consequently, it is possible to obtain an advantage that the whole light emitting diodes 2 can be disposed to overlap with the light guiding plate 5 in a horizontal direction (alternatively, only a part of the light emitting diodes 2 may overlap) and the size of the lighting apparatus for an inspection can be reduced in the vertical direction. On the other hand, a large number of light emitting diodes 2 may be provided below the light guiding plate 5 (in a non-overlapping position). The shape of the light guiding plate 5 can be changed depending on the shape of the inspection object, for example, to take the shape of a circle, a rectangle, a triangle, an ellipse or the like.

The lighting apparatus for an inspection can mainly be used for aiding to attach an electronic component to a substrate in addition to the inspection of the scratches of the external appearance of a product and the inspection of a product such as the quality of soldering of a substrate in a factory, an inspection room and the like. As described above, an image caught by the CCD camera 7 may be processed by an image processing device which is not shown and the quality of the image may be thus determined by a computer, or the image may be projected onto a monitor screen or the like to determine the quality by operator-watching. The CCD camera 7 may be omitted to check the inspection object 4 by only visual observation.

The light guiding plate 5 constitutes a member for diffusing and transferring an incident light, and is preferred to have a higher transparency to transmit a light in a larger amount. However, the light guiding plate 5 may have an available low transparency within the range capable of working the invention. Concavo-convex portions may be formed on an emitting surface (the lower surface shown in FIG. 1A) 5A of the light guiding plate 5 by embossing in such a manner that a light can be emitted and diffused from the emitting surface 5A to have a uniform luminous intensity. Moreover, smaller concavo-convex portions (wrinkles or satin finished surface) than the concavo-convex portions subjected to the embossing may be provided by graining, thereby taking the shape of a frosted glass surface to have a more uniform luminous intensity. However, it can not be always necessary to process the concavo-convex surface described above. Furthermore, a transparent member may be a lens or a simple glass which can collect and diverge a light other than the light guiding plate 5.

Figure 1B:
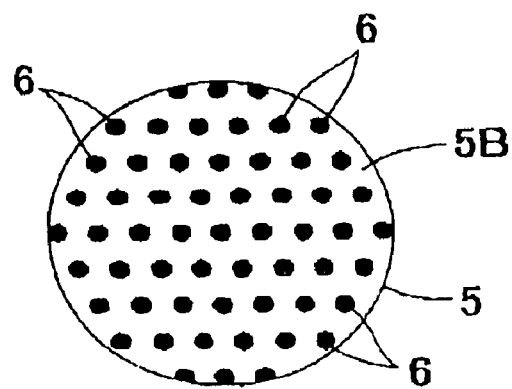

As shown in FIGS. 1A and 1B, a white paint is directly put as like dotted pattern with spots at a predetermined interval over a surface 5B of the light guiding plate 5 facing the CCD cameral 7, which is shown as the upper surface in FIG. 1A, thereby constituting the reflecting portion 6 having a light diffusively reflecting property (which is blackened for easy understanding in FIG. 1B). Accordingly, the light incident upon the reflecting portion 6 is reflected in part toward the inspection object 4, and furthermore, the light reflected by the inspection object 4 in part can be fetched into the CCD camera 7 through the upper surface area of the light guiding plate 5 in which the reflecting portion 6 is not present, that is, apertures among the reflecting portions. The shape and size of the reflecting portion 6 and the distance between the adjacent reflecting portions 6 and 6 can be freely changed if the light can be appropriately fetched into the CCD camera 7 to carry out a preferrable image processing. Moreover, the upper surface 5B of the light guiding plate 5 may be directly provided with the reflecting portion 6 by pattern forming means using screen printing, photoprinting, a projection type exposing device or the like, or a concavo-convex processing such as graining or embossing. In addition, a separate transparent film (not shown) from the light guiding plate 5 can be provided with the reflecting portion 6 and such transparent film with the reflecting portion can be laid on the upper surface of the light guiding plate 5.

Figure 4:
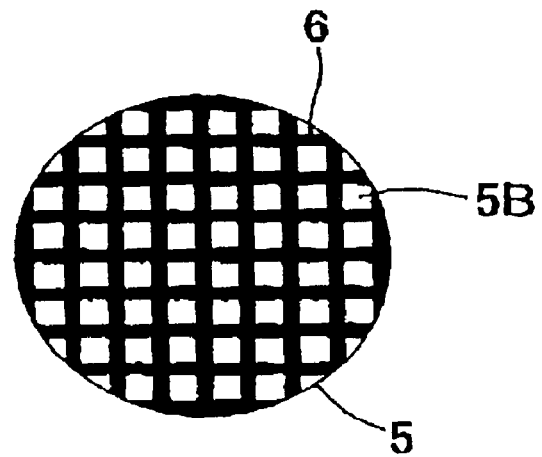
FIG. 4 is a plan view showing another light guiding plate having another construction of the reflecting portion.

As shown in FIG. 4, the reflecting portions 6 may be constituted like a grid with straight lines at regular intervals in each of intersectional directions. In this case, each portion not occupied by straight line is almost square. By exchanging the straight line into a curved line, it is also possible to take any shape such as a circle, an ellipse, a rhombus or a triangle.

Figure 2:
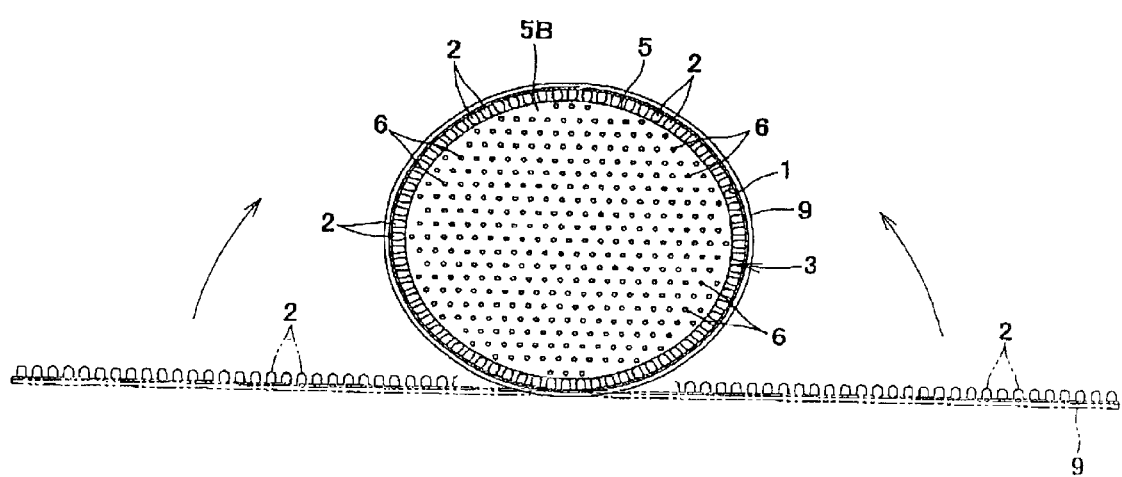
FIG. 2 is a view illustrating a state in which a substrate having a light emitting diodes fixed thereon is attached to a light guiding plate.

Each of the light emitting diodes 2 is attached to a band-like plate substrate 9 having a flexibility as shown by a chain double-dashed line in FIG. 2, and the substrate 9 are bent up to abut both ends of the whole length thereof as shown in FIG. 2 so that the circular substrate 9 can be constituted. Thus, there is an advantage that a large number of light emitting diodes 2 can easily be attached onto the substrate 9 on the same plane. It is also possible to employ such a construction that each of the light emitting diodes 2 is attached to the inner surface of the substrate 9 previously constituted circularly. Moreover, the substrate 9 may take any shape such as a circle, an ellipse, a square or a trapezoid seen on a plane. The shape of the light guiding plate 5 is changed according to the shape of the substrate 9.

Figure 3:
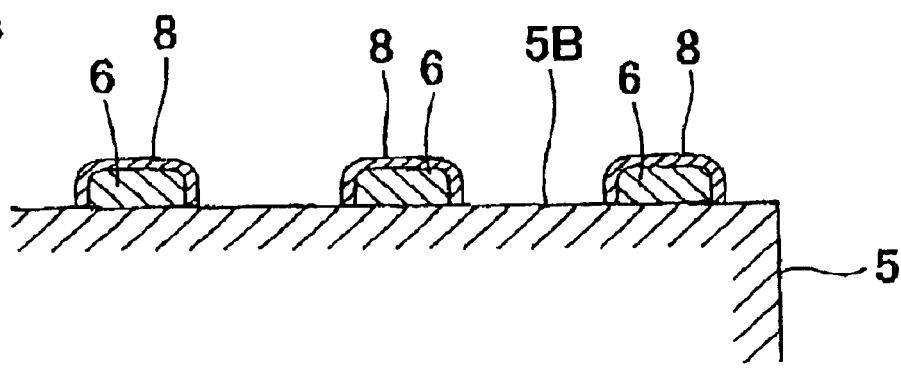
FIG. 3 is a longitudinal sectional view showing the main part of the light guiding plate.

As shown in FIG. 3, a layer 8 having such a color as to absorb a light, for example, a black or near black is provided on the upper surface of each of the reflecting portions 6. Consequently, it is possible to eliminate a drawback that a light is diffusively reflected by the top surface of the white reflecting layer 6 and image recognition by the image input means (the CCD camera 7) become difficult. In the case in which the reflecting portion 6 is constituted by aluminum evaporation and can be totally reflected, the layer 8 can be omitted.

Figure 5:
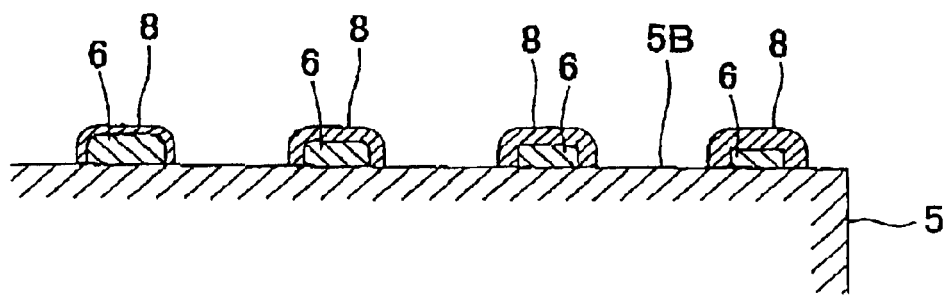
FIG. 5 is a longitudinal sectional view showing the main part of the light guiding plate having the structure of another reflecting portion.
Figure 6:
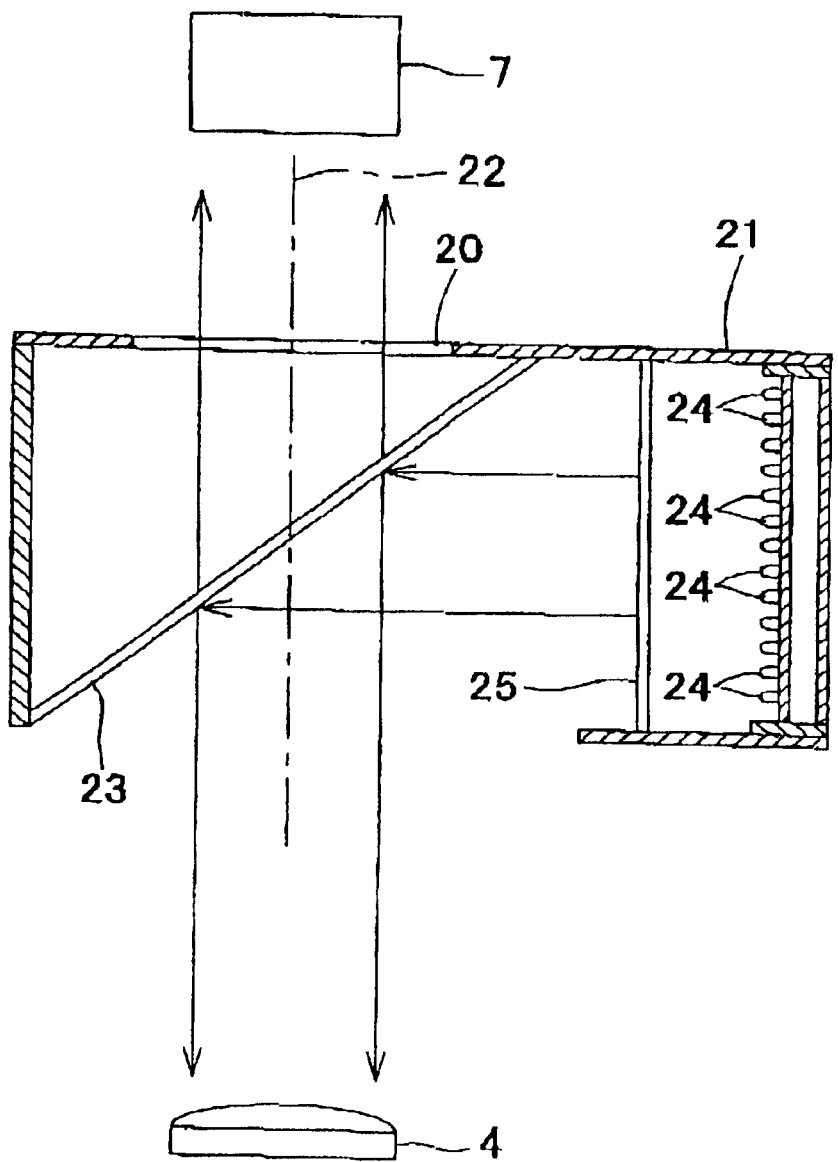
FIG. 6 is a longitudinal sectional view showing a conventional lighting apparatus for an inspection.

FIG. 3 shows the case in which each of the reflecting portions 6 having the same area is provided over the whole region of the upper surface of the light guiding plate 5. As shown in FIG. 5, the area of the reflecting portion 6 may be gradually reduced from one facing the center of the CCD camera 7 to the others facing an outer peripheral edge (into three gradations or more, for example, four gradations in the drawing), thereby acquiring a visual field having the same brightness in all the portions of the lens. As described above, there is an advantage that it is possible to obtain a visual field having the same brightness in all the portions of the lens still more by gradually reducing the area of the reflecting portion 6 from one facing the center of the CCD camera 7 to the others facing the outer peripheral edge. The reflecting portion 6 can also be classified into two sizes. More specifically, the reflecting portions are divided into a central part reflecting portion 6 positioned in a part corresponding to the center of the camera 7 and the other portions not corresponding to the center of the camera 7, that is, outer peripheral reflecting portions 6 positioned corresponding to an outer peripheral edge, and the area of each of the outer peripheral reflecting portion 6 is more decreased than that of each of the central reflecting portions 6.

While as shown in FIGS. 1A and 2, the light emitting diodes 2 are provided in only one line along the horizontal direction of the substrate 9, it maybe disposed in a plurality of parallel lines along the horizontal direction in order to increase an amount of irradiation. For the light emitting diode 2, it is also possible to use a combination of light emitting diodes for emitting respective lights of R, G, B in addition to white light emitting diodes or light emitting diodes to be selected for full colors. Moreover, it is also possible to divide a large number of light emitting diodes 2 into a plurality of groups and to emit a light from each group one after another to carry out an inspection in addition to an inspection to be performed by emitting a light from all the light emitting diodes 2.

By constituting the light guiding plate 5 by a flat member, it is possible to more reduce the size of a lighting apparatus for an inspection in the vertical direction. For example, the light guiding plate 5 may be of a dome type which takes the longitudinal sectional shape of a semicircle and has an opened lower part. In this case, the inner surface of the dome type light guiding plate is provided with a large number of reflecting portions, while a large number of light emitting diodes for irradiating a light onto the reflecting portions are mounted circularly to irradiate the light reflected by the reflecting portions onto the inspection object put in a lower position. Moreover, the outer surface of the dome type light guiding plate is caused to include a large number of reflecting portions, while a large number of light emitting diodes to irradiate upward are provided with lighting surfaces disposed on the lower end face of the light guiding plate, and lights emitted from the light emitting diodes are guided by the light guiding plate and a part of the lights thus guided is reflected by the reflecting portion and is thereby applied on the inspection object in the lower position. Moreover, the light guiding plate to be used may be of a dome type having a semicircular longitudinal section, and furthermore, may be of a modified dome type having an arch-shaped longitudinal section. In this case, the inner surface or outer surface of an upper plate portion constituting the light guiding plate is provided with a large number of reflecting portions, while a large number of light emitting diodes are attached to a circular support member fixed to the inner surface of the lower end of a vertical plate portion which is downwardly provided from the outer peripheral edge of the upper plate portion, and the lights emitted from the light emitting diodes are reflected by the reflecting portion and thus applied on the inspection object put in the lower part.

According to the first aspect of the invention, a large number of light emitters can be provided circularly and the size of the whole lighting apparatus can be reduced in the vertical direction as compared with a conventional apparatus in which the light emitters are provided in only a position laterally opposed to a half mirror. In addition, the light emitted from the light emitters provided circularly is guided through the guide member to the inspection object provided in the lower part. Consequently, it is possible to omit a diffusion plate which is required for the conventional art. Thus, it is possible to provide a small or size-reduced lighting apparatus for an inspection.

According to the second aspect of the invention, the guide member is a flat and transparent light guiding plate, and a surface on an opposite side to the inspection object of the light guiding plate is caused to include a dotted pattern with white painted spots or a white painted grid pattern directly thereon or over a transparent film provided on the surface, or a concavo-convex configuration is formed directly over the surface or over the transparent film provided on the surface, thereby constituting reflecting portion with a light diffusing property. Consequently, it is possible to reduce the size of the guide member in the vertical direction, and furthermore, to cause the amount of irradiation of the light to be uniform in any portion of the inspection object. Thus, precision in an inspection can be enhanced.

According to the third aspect of the invention, the upper surface of the reflecting portion is covered with the layer for absorbing a light. Consequently, it is possible to avoid such a situation that the light is diffusively reflected by the upper surface of the reflecting portion, resulting in the difficult recognition of the image input means. Thus, the precision in an inspection can be enhanced.

According to the fourth aspect of the invention, the areas of the reflecting portions positioned remote from the image input means are more reduced than those of the other reflecting portions near the image input means. Consequently, it is possible to obtain a visual field having substantially the same brightness in all the portions of the lens. Thus, the precision in an inspection can be uniformed irrespective of inspecting portions.

What is claimed is:

1. A lighting apparatus for inspection of an object, comprising:
   a) a large number of light emitters arranged in a circle in a horizontal plane above the object to be inspected; and
   b) a light guiding means arranged inside the circle of the light emitters for downwardly directing a part of light emitted from the light emitters to the object to be inspected for reflection therefrom, and upwardly passing light reflected by the object to be inspected, the light guiding means comprising a flat and transparent light guiding plate having opposite sides and provided with a large number of reflecting portions on at least one of the sides, both sides of the light guiding plate extending in parallel with the horizontal plane, the reflecting portions being arranged with a distance therebetween for downwardly directing the part of the light emitted from the light emitters, the light guiding means allowing the light reflected by the object to be inspected to pass through apertures among the reflecting portions.

2. The lighting apparatus for inspection of an object according to claim 1, wherein the light guiding plate has, as the reflecting portions, a dotted pattern with white painted spots or a white painted grid pattern, or a transparent film provided with the dotted pattern with white painted spots or the white painted grid pattern on its surface at a side departing from the object, or having a concavo-convex configuration or a transparent film provided with the concavo-convex configuration on its surface at a side departing from the object.

3. The lighting apparatus for inspection of an object according to claim 1, wherein an upper surface of each of the reflecting portions is covered with a light absorbing layer.

4. The lighting apparatus for inspection of an object according to claim 2, wherein the light emitters comprise light emitting diodes arranged along an outer peripheral edge of the light guiding plate for emitting the light in a direction toward a center of the light guiding plate, and wherein a cross-sectional area of each of the light emitting diodes substantially corresponds to a thickness of the light guiding plate.

5. The lighting apparatus for inspection of an object according to claim 1, wherein areas of the reflecting portions decrease in proportion to a distance from an imaging device receiving the light for inspection.

* * * * *